(12) United States Patent
Tung et al.

(10) Patent No.: US 8,188,278 B2
(45) Date of Patent: *May 29, 2012

(54) PHOTOSENSITIZER DYE AND DYE SENSITIZED SOLAR CELL

(75) Inventors: Yung-Liang Tung, Hualien County (TW); Kai-Lin Ou, Taipei County (TW); Chun-Guey Wu, Hualien County (TW); Chia-Yuan Chen, Chiayi (TW); Shi-Jhang Wu, Taipei County (TW); Jheng-Ying Li, Taoyuan County (TW); Song-Yeu Tsai, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 332 days.

This patent is subject to a terminal disclaimer.

(21) Appl. No.: 12/484,249

(22) Filed: Jun. 15, 2009

(65) Prior Publication Data

US 2010/0099873 A1     Apr. 22, 2010

(30) Foreign Application Priority Data

Oct. 17, 2008   (TW) ................................ 97140055 A
May 27, 2009   (TW) ................................ 98117801 A (51) Int. Cl.
    *C07F 15/00* (2006.01)
    *H01L 31/042* (2006.01)
(52) U.S. Cl. .............................. 546/2; 136/263; 136/252
(58) Field of Classification Search ........ 546/2; 136/252, 136/263
    See application file for complete search history.

(56) References Cited

U.S. PATENT DOCUMENTS 7,645,879 B2 * 1/2010 Wu et al. ........................ 546/2

OTHER PUBLICATIONS

Article Titled "Multifunctionalized Ruthenium-Based Supersensitizers for Highly Efficient Dye-Sensitized Solar Cells" authored by Chia-Yuan Chen et al, in Angew. Chem Int. Ed. 2008, 47, pp. 7342-7345.

* cited by examiner

*Primary Examiner* — Charanjit Aulakh
(74) *Attorney, Agent, or Firm* — Jianq Chyun IP Office (57) ABSTRACT

A photosensitizer dye is provided and it is a ruthenium-based complex represented by formula (1):

Formula (1)

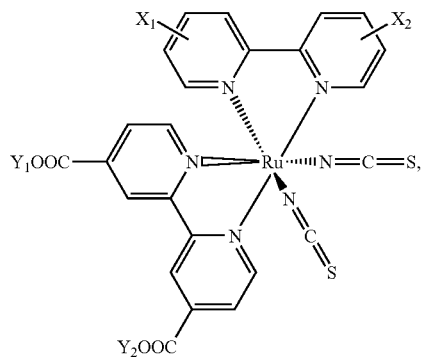

wherein $X_1$ is one of formulae (2) to (7) and $X_2$ is hydrogen (H) or the same as $X_1$.

12 Claims, 1 Drawing Sheet

PHOTOSENSITIZER DYE AND DYE SENSITIZED SOLAR CELL

CROSS-REFERENCE TO RELATED APPLICATION

This application claims the priority benefit of Taiwan application serial no. 97140055, filed Oct. 17, 2008 and serial no. 98117801, filed on May 27, 2009. The entirety of each of the above-mentioned patent applications is hereby incorporated by reference herein and made a part of specification.

BACKGROUND OF THE INVENTION

1. Field of Invention

The present invention relates to a photosensitizer dye suitable for a dye-sensitized solar cell (DSSC).

2. Description of Related Art

Currently, the seeking and development of non-polluting renewable energies (or so-called green energies) has become one of the important topics. Among various renewable energies, solar energy is a non-polluting and useless energy, so that how to effectively use solar energy has always been the focus when solving the problems caused from the pollutions and shortages of petroleum energies. Solar cell which can directly convert solar energy into electricity has become the key issue in the current application of solar energy.

Recently, since Grätzel and O'Regan proposed a new type solar cell, i.e. so-called dye-sensitized solar cell (DSSC), such solar cell has caused the attention in the industry due to the advantages of effective conversion from solar energy to electricity and low fabrication cost of the cell device. Generally speaking, the structure of a DSSC includes four parts as follows: cathode/anode electrodes respectively providing current flow paths, a semiconductor such as $TiO_2$ accepting the electrons, a dye molecule layer absorbed to the semiconductor and electrolyte for transporting the holes. The device efficiency is affected by the material of each part and the interface structures between the parts in the DSSC, wherein the dye used for the dye molecule layer affects the efficiency of the DSSC most.

Therefore, seeking dye molecules which enable the DSSC to achieve effective photoelectric conversion has become one of the main topics in the current development.

SUMMARY OF THE INVENTION

Accordingly, the present invention is directed to a new type photosensitizer dye having good light-absorbing ability, i.e. the absorption spectrum thereof similar to the solar light spectrum.

The present invention is further directed to a DSSC including the above-mentioned photosensitizer dye that can absorb solar light effectively, so that good photoelectric conversion efficiency thereof is achieved.

The present invention provides a photosensitizer dye. The photosensitizer dye is a ruthenium-based complex represented by formula (1):

Formula (1)

(1)

wherein $X_1$ is represented by formula (2); and $X_2$ is hydrogen or the same as $X_1$.

Formula (2)

(2)

wherein Ra and Rb are each independently hydrogen, $C_mH_{2m+1}$ with m from 1 to 15 or $OC_pH_{2p+1}$ with p from 1 to 15; and n is from 1 to 4;

wherein $Y_1$ is hydrogen, lithium (Li), sodium (Na) or a tetra-alkyl ammonium group represented by formula (8); and $Y_2$ is hydrogen or the same as $Y_1$.

Formula (8)

(8)

wherein A, B, C and D are each independently hydrogen or $C_mH_{2m+1}$ with m from 1 to 15.

The present invention further provides a photosensitizer dye. The photosensitizer dye is a ruthenium-based complex represented by formula (1):

Formula (1)

wherein $X_1$ is represented by formula (3); and $X_2$ is hydrogen or the same as $X_1$.

Formula (3)

wherein Rc is hydrogen or $C_mH_{2m+1}$ with m from 1 to 15; Rd and Re are each independently $C_mH_{2m+1}$ with m from 1 to 15 or $OC_pH_{2p+1}$ with p from 1 to 15; and n is from 1 to 4;
wherein $Y_1$ is hydrogen, lithium, sodium or a tetra-alkyl ammonium group represented by formula (8); and $Y_2$ is hydrogen or the same as $Y_1$.

Formula (8)

wherein A, B, C and D are each independently hydrogen or $C_mH_{2m+1}$ with m from 1 to 15.

The present invention further provides a photosensitizer dye. The photosensitizer dye is a ruthenium-based complex represented by formula (1):

Formula (1)

wherein $X_1$ is represented by formula (4); and $X_2$ is hydrogen or the same as $X_1$.

Formula (4)

wherein Rf, Rg and Rh are each independently hydrogen, $C_mH_{2m+1}$ with m from 1 to 15 or $OC_pH_{2p+1}$ with p from 1 to 15; and n is from 1 to 4;
wherein $Y_1$ is hydrogen, lithium, sodium or a tetra-alkyl ammonium group represented by formula (8); and $Y_2$ is hydrogen or the same as $Y_1$.

Formula (8)

wherein A, B, C and D are each independently hydrogen or $C_mH_{2m+1}$ with m from 1 to 15.

The present invention further provides a photosensitizer dye. The photosensitizer dye is a ruthenium-based complex represented by formula (1):

Formula (1)

wherein $X_1$ is represented by formula (5); and $X_2$ is hydrogen or the same as $X_1$.

Formula (5)

wherein Ri, Rj and Rk are each independently hydrogen, $C_mH_{2m+1}$ with m from 1 to 15 or $OC_pH_{2p+1}$ with p from 1 to 15; and n is from 1 to 4;
wherein in formula (1), $Y_1$ is hydrogen, lithium, sodium or a tetra-alkyl ammonium group represented by formula (8); and $Y_2$ is hydrogen or the same as $Y_1$.

Formula (8)

$$D-\overset{A}{\underset{C}{\overset{\oplus}{N}}}-B,\quad(8)$$

wherein A, B, C and D are each independently hydrogen or $C_mH_{2m+1}$ with m from 1 to 15.

The present invention further provides a photosensitizer dye. The photosensitizer dye is a ruthenium-based complex represented by formula (1):

Formula (1)

[Structure of ruthenium complex with X₁, X₂, Y₁OOC, Y₂OOC, Ru, N=C=S, NCS groups] (1)

wherein $X_1$ is represented by formula (6); and $X_2$ is hydrogen or the same as $X_1$;

Formula (6)

[Structure with thiophene ring, fluorene group, Rl, Rm, Rn, Ro substituents] (6)

wherein Rl, Rm, Rn and Ro are each independently hydrogen, $C_mH_{2m+1}$ with m from 1 to 15 or $OC_pH_{2p+1}$ with p from 1 to 15; and n is from 1 to 4;

wherein $Y_1$ is hydrogen, lithium, sodium or a tetra-alkyl ammonium group represented by formula (8); and $Y_2$ is hydrogen or the same as $Y_1$.

Formula (8)

$$D-\overset{A}{\underset{C}{\overset{\oplus}{N}}}-B,\quad(8)$$

wherein A, B, C and D are each independently hydrogen or $C_mH_{2m+1}$ with m from 1 to 15.

The present invention further provides a photosensitizer dye. The photosensitizer dye is a ruthenium-based complex represented by formula (1):

Formula (1)

[Structure of ruthenium complex] (1)

wherein $X_1$ is represented by formula (7); and $X_2$ is hydrogen or the same as $X_1$;

Formula (7)

[Structure with thiophene ring, dibenzothiophene group, Rp, Rq substituents] (7)

wherein Rp is hydrogen, $C_mH_{2m+1}$ with m from 1 to 15 or $OC_pH_{2p+1}$ with p from 1 to 15; Rq is $C_mH_{2m+1}$ with m from 1 to 2 or $OC_pH_{2p+1}$ with p from 1 to 15; and n is from 1 to 4;

wherein $Y_1$ is hydrogen, lithium, sodium or a tetra-alkyl ammonium group represented by formula (8); and $Y_2$ is hydrogen or the same as $Y_1$.

Formula (8)

$$D-\overset{A}{\underset{C}{\overset{\oplus}{N}}}-B,\quad(8)$$

wherein A, B, C and D are each independently hydrogen or $C_mH_{2m+1}$ with m from 1 to 15.

The present invention further provides a DSSC, in which one of the above-mentioned photosensitizer dyes is used as the material of the dye layer.

In the present invention, the ruthenium-based complex photosensitizer dye has at least one of the special groups represented by formulae (2) to (8), so that the ruthenium-based complex photosensitizer dye has good light-absorbing ability and the absorption spectrum thereof is similar to the solar light spectrum. Further, the fabricated DSSC including the ruthenium-based complex photosensitizer dye of the present invention has good photoelectric conversion efficiency.

In order to make the aforementioned and other objects, features and advantages of the present invention comprehensible, a preferred embodiment accompanied with figures is described in detail below.

DESCRIPTION OF EMBODIMENTS

A photosensitizer dye of the present invention is a ruthenium-based complex represented by the following chemical formula (1):

Formula (1)

wherein in formula (1), $X_1$ is one of formulae (2) to (7); $X_2$ is hydrogen or the same as $X_1$; $Y_1$ is hydrogen, lithium, sodium or a tetra-alkyl ammonium group represented by formula (8); and $Y_2$ is hydrogen or the same as $Y_1$.

Formula (8)

wherein in formula (8), A, B, C and D are each independently hydrogen or $C_mH_{2m+1}$ with m from 1 to 15.

In an embodiment, $X_1$ is represented by formula (2), and $X_2$ is hydrogen or the same as $X_1$.

Formula (2)

wherein Ra and Rb are each independently hydrogen, $C_mH_{2m+1}$ with m from 1 to 15 or $OC_pH_{2p+1}$ with p from 1 to 15; and n is from 1 to 4.

In an embodiment, $X_1$ is represented by formula (3), and $X_2$ is hydrogen or the same as $X_1$.

Formula (3)

wherein Rc is hydrogen or $C_mH_{2m+1}$ with m from 1 to 15; Rd and Re are each independently $C_mH_{2m+1}$ with m from 1 to 15 or $OC_pH_{2p+1}$ with p from 1 to 15; and n is from 1 to 4.

In an embodiment, $X_1$ is represented by formula (4), and $X_2$ is hydrogen or the same as $X_1$.

Formula (4)

wherein Rf, Rg and Rh are each independently hydrogen, $C_mH_{2m+1}$ with m from 1 to 15 or $OC_pH_{2p+1}$ with p from 1 to 15; and n is from 1 to 4.

In an embodiment, $X_1$ is represented by formula (5), and $X_2$ is hydrogen or the same as $X_1$.

Formula (5)

wherein Ri, Rj and Rk are each independently hydrogen, $C_mH_{2m+1}$ with m from 1 to 15 or $OC_pH_{2p+1}$ with p from 1 to 15; and n is from 1 to 4.

In an embodiment, $X_1$ is represented by formula (6), and $X_2$ is hydrogen or the same as $X_1$.

Formula (6)

wherein Rl, Rm, Rn and Ro are each independently hydrogen, $C_mH_{2m+1}$ with m from 1 to 15 or $OC_pH_{2p+1}$ with p from 1 to 15; and n is from 1 to 4.

In an embodiment, X1 is represented by formula (7), and $X_2$ is hydrogen or the same as $X_1$.

Formula (7)

wherein Rp is hydrogen, $C_mH_{2m+1}$ with m from 1 to 15 or $OC_pH_{2p+1}$ with p from 1 to 15; Rq is $C_mH_{2m+1}$ with m from 1 to 2 or $OC_pH_{2p+1}$ with p from 1 to 15; and n is from 1 to 4.

In the present invention, the ruthenium-based complex photosensitizer dye has at least one of the special groups represented by formulae (2) to (8), so that the ruthenium-based complex photosensitizer dye has good light-absorbing ability and the absorption spectrum thereof is similar to the solar light spectrum. Therefore, when the ruthenium-based complex photosensitizer dye of the present invention is applied to the DSSC, the solar light can be effectively accepted and converted into electric currents.

The synthesis examples of the ruthenium-based complex photosensitizer dyes of the present invention are introduced in the following. However, the following examples are provided for illustration purposes and are not construed as limiting the present invention.

EXAMPLES

The synthesis example is illustrated by two of the ruthenium-based complexes of the present invention. The two ruthenium-based complexes are respectively CYC-B6L represented by formula (1-1) and CYC-B7 represented by formula (1-2).

Formula (1-1)

CYC-B6L

CYC-B7

CYC-B6L is obtained when $X_1$ and $X_2$ are the same group in formula (1) and $X_1$ is represented by formula (3), wherein in formula (3), Rc is hydrogen, Rd is $C_7H_{15}$, Re is $C_7H_{15}$ and n is 1; and in formula (1), $Y_1$ is hydrogen and $Y_2$ is the same as $Y_1$. CYC-B7 is obtained when $X_1$ and $X_2$ are the same group in formula (1) and $X_1$ is represented by formula (3), wherein in formula (3), Rc is hydrogen, Rd is $C_7H_{15}$, Re is $C_7H_{15}$ and n is 2; and in formula (1), $Y_1$ is hydrogen and $Y_2$ is the same as $Y_1$.

The process is started from the preparation of the ligands, and the synthesis process is shown in the process flow I.

-continued 7. n = 1
8. n = 2

Process Flow I: Preparation of Ligands
The Synthesis Process of the Ligands is Described Below:

(1) 36.75 g (0.2 mol) of heptanoyl chloride were added to 18 g (0.1 mol) of carbazole ($C_{12}H_9N$) and 31.605 g of $AlCl_3$ in ice bath, dehydrated solvent $CS_2$ was then added, and the mixture was reacted for 4 hours. Thereafter, the solvent was removed, and a mixture of ice and water was added to precipitate the product. Afterwards, ethyl acetate (EA) was used for re-crystallization, so as to further purify the product. Finally, the compound 1 was obtained and the yield was 41%.

(2) 4.3 g of zinc powder, 0.43 g (1.58 mmol) of mercury (II) chloride ($HgCl_2$), 0.2 ml of HCl and 5.5 ml of water were placed into a round bottom flask and stirred for several minutes to obtain a heterogeneous solution. The solvent was then removed as much as possible. Thereafter, 2.7 ml of water, 0.65 ml of HCl, 20 ml of toluene and 1.95 g (0.005 mol) of the compound 1 were added, and the mixture was heat refluxed for 30 hours. During the reaction period of 30 hours, 1.8 ml of HCl was added every 6 hours. After the reaction was completed, ether was added for extraction and the organic layer was collected. The collected organic layer was dehydrated by anhydrous $MgSO_4$ to remove water, filtered and rotary concentrated to remove most of the organic solvent. Afterwards, column chromatography was used for further purification. Finally, the compound 2 was obtained and the yield was 70.2%.

(3) 6.04 g (16.6 mmol) of the compound 2, 2.98 g (21.56 mmol) of $K_2CO_3$, 3.06 g (16.6 mmol) of Cu-bronze and 3.25 g (19.92 mmol) of 2-bromothiopene ($C_4H_3BrS$) (for preparing the ligands of CYC-B6L) or 4.9 g (19.92 mmol) of 2-bromo-5 (thiophen-2-yl)thiophene (for preparing the ligands of CYC-B7) were placed in a side-arm round bottom flask. Nitrobenzene ($C_6H_5NO_2$) was added, and the mixture was refluxed for 18 hours in nitrogen atmosphere. Thereafter, the solvent was removed, ammonium was added, and the mixture was stirred for 2 hours. A large amount of water and $CHCl_3$ were added for extraction, and the organic layer was collected. The collected organic layer was dehydrated by anhydrous $MgSO_4$ to remove water, filtered and rotary concentrated to remove most of the organic solvent. Afterwards, column chromatography was used for further purification. Finally, the compound 3 with the yield of 38% or the compound 4 with the yield of 30% was obtained.

(4) 2.83 g of the compound 3 or 3.42 g of the compound 4 was placed in a side-arm round bottom flask, and 35 ml of anhydrous tetrahydrofuran (THF) was added. Ethanol and liquid nitrogen were used to control the temperature of the side-arm round bottom flask at −78° C., and 2.54 ml (for the flask containing the compound 3) or 3.1 ml (for the flask containing the compound 4) of n-butyl lithium (n-BuLi) (2.5 M in hexane) was slowly injected, and the mixture was stirred for 2 hours after the temperature was back to the room temperature naturally. Thereafter, 1.27 g (for the flask containing the compound 3) or 1.7 g (for the reaction flask the compound 4) of $Me_3SnCl$ was slowly injected, and the mixture was stirred for 10 hours after the temperature was back to the room temperature naturally. Afterwards, a large amount of wafer and dichloromethane ($CH_2Cl_2$) were added for extraction. The collected organic layer was extracted again rapidly with saturated NaCl solution and then rotary concentrated to remove the organic solvent. Finally, the compound 5 or the compound 6 was obtained.

(5) 3.6 g of the compound 5 or 4.68 g of the compound 6 and 0.9 g or 0.96 of 4,4'-dibromo-2,2'-bipyridine were placed in a side-arm round bottom flask and vacuum stirred for 30 minutes. Thereafter, 40 ml of anhydrous dimethylformamide (DMF) was added. The following steps are repeated 3 to 4 times: controlling the temperature of the side-arm round bottom flask at −78° C., vacuum pumping for 5-10 minutes, waiting the temperature back to the room temperature and introducing Ar after DMF was resolved, so as to make sure that the flask was oxygen-free. In Ar atmosphere, 0.4 g or 0.43 g of $Pd(PPh_3)_4$ catalyst which had been resolved by a very small amount of THF was injected into the side-arm found bottom flask with a dry bridge needle, the flask was set up on the reflux apparatus, and the mixture was heated at 160° C. for 72 hours. After the reaction was completed, saturated $NH_4Cl_{(aq)}$ was added and the mixture was stirred for 10 minutes to end the reaction. $CH_2Cl_2$ was then added for extraction. The impurities of the collected organic layer were extracted respectively by $NaHCO_{3(aq)}$, DI water and saturated NaCl. The organic layer was dehydrated by anhydrous $MgSO_4$ to remove water, filtered and rotary concentrated to remove most of the organic solvent. Soxhlet including removing the impurities with n-hexane and then resolving the product with EA was used for further purification of the product. Finally, the compound 7 with the yield of 60% or the compound 8 with the yield of 73.1% was obtained. The mass spectrographic ideal value of the compound 7 was m/z 1043 ([M]$^+$), and the actual value (LRMS(FAB)) of the same was m/z 1043.4 (m) ([M]$^+$). The mass spectrographic ideal value of the compound (8) was m/z 1206.6 ([M]$^+$), and the actual value (LRMS(FAB)) of the same was m/z 1207.2 (m) ([M]$^|$).

The synthesis process of dye molecules of the present invention is adopting a one-pot method with the synthesized ligands. The synthesis process is described in the following process flow II.

Process Flow II: Preparation of Dye Molecules
The Synthesis Process of the Dye Molecules is Described Below:

(6) The synthesis of CYC-B6L:

0.45 g of [RuCl$_2$(p-cymene)]$_2$, 1.53 g of the compound 7 were placed in a three-neck round-bottom flask, anhydrous DMF was added, and the mixture was heated to 80° C. and reacted for 4 hours in Ar atmosphere. Thereafter, 0.36 g of dcbpy (4,4'-dicarboxylic acid-2,2'-bipyridine) was added and the mixture was reacted for 4 hours with the reaction temperature controlled at 160° C. The light was blocked out to avide producing the isomer. Excessive NH$_4$NCS was then added and the mixture was reacted for 5 hours with the temperature dropping to 130° C. The solvent was removed by using a vacuum system, and water was added to remove the unreacted NH$_4$NCS. The solids were collected by gas filtering. Afterwards, the solids were sequentially washed with DI water and ether and then vacuum dried. The solids were resolved by methanol and further purified with column chromatography by using methanol as eluent. The main fractions were collected, rotary concentrated to remove methanol and acidified by 0.01 M of nitric acid solution, so as to obtain purple-black solids. The mass spectrographic ideal value of the solids was m/z 1504.5 ([M]$^+$, and the actual value (LRMS (FAB)) of the same was m/z 1504.3 (m) ([M]$^+$).

(7) The synthesis of CYC-B7:

0.45 g of [RuCl$_2$(p-cymene)]$_2$, 1.53 g of the compound 7 were placed in a three-neck round bottom flask, anhydrous DMF was added, and the mixture was heated to 80° C. and reacted for 4 hours in Ar atmosphere. Thereafter, 0.55 g of dcbpy (4,4'-dicarboxylic acid-2,2'-bipyridine) was added and the mixture was reacted for 4 hours with the reaction temperature controlled at 160° C. The light was blocked out to avide producing the isomer. Excessive NH$_4$NCS was then added and the mixture was reacted for 5 hours with the temperature dropping to 130° C. The solvent was removed by using a vacuum system, and water was added to remove the unreacted NH$_4$NCS. The solids were collected by gas filtering. Afterwards, the solids were sequentially washed with DI water and ether and then vacuum dried. The solids were resolved by methanol and further purified with column chromatography by using methanol as eluent. The main fractions were collected, rotary concentrated to remove methanol and acidified by 0.01 M of nitric acid solution, so as to obtain purple-black solids. The mass spectrographic ideal value of the solids was m/z 1668.5 ([M]$^+$, and the actual value (LRMS (FAB)) of the same was m/z 1668.1 (m) ([M]$^+$).

The absorption coefficient measurement of the photosensitizer dyes of the present invention is introduced in the following. The absorption coefficients of CYC-B6L and CYC-B7 are compared with those of the conventional photosensitizer dyes. The absorption coefficient measurement of the photosensitizer dyes of the present invention includes preparing a photosensitizer dye solution of a predetermined concentration, placing an appropriate amount of the solution in a quartz sample tank, and putting the quartz sample tank in a UV/Vis absorption spectrometer to perform an analysis and measurement. The Beer's law (A=ϵbc) is used to calculate the absorption coefficient. The absorption coefficients of CYC-B6L and CYC-B7 are compared with those of the conventional photosensitizer dyes, and the measurement results are shown in Table 1.

The conventional photosensitizer dyes in Table 1 are respectively "N3" mentioned in M. K. Nazeeruddin et al., *J. Am. Chem. Soc.* 1993, 115, 6382, and "Black dye" mentioned in M. K. Nazeeruddin et al., *J. Am. Chem. Soc.*, 2001, 123, 1613.

TABLE 1

| | Photosensitizer dye | | | |
|---|---|---|---|---|
| | CYC-B6L | CYC-B7 | N3 | Black dye |
| Absorption peak at the longest wavelength & Absorption coefficient ($*10^{-3}$ M$^{-1}$ cm$^{-1}$) | 551 nm (16.3) | 552 nm (21.9) | 530 nm (14.5) | 600 nm (7.64) |

As shown in Table 1, the absorption coefficients of CYC-B6L and CYC-B7 of the present invention are higher than those of the conventional photosensitizer dyes. That is, the ruthenium-based complex photosensitizer dye of the present invention has at least one of the special groups represented by formulae (2) to (8), so that the absorption coefficient thereof is higher than that of the conventional photosensitizer dyes. Accordingly, when the ruthenium-based complex photosensitizer dye of the present invention is applied to the DSSC, good photoelectric conversion efficiency is obtained.

Figure 1:
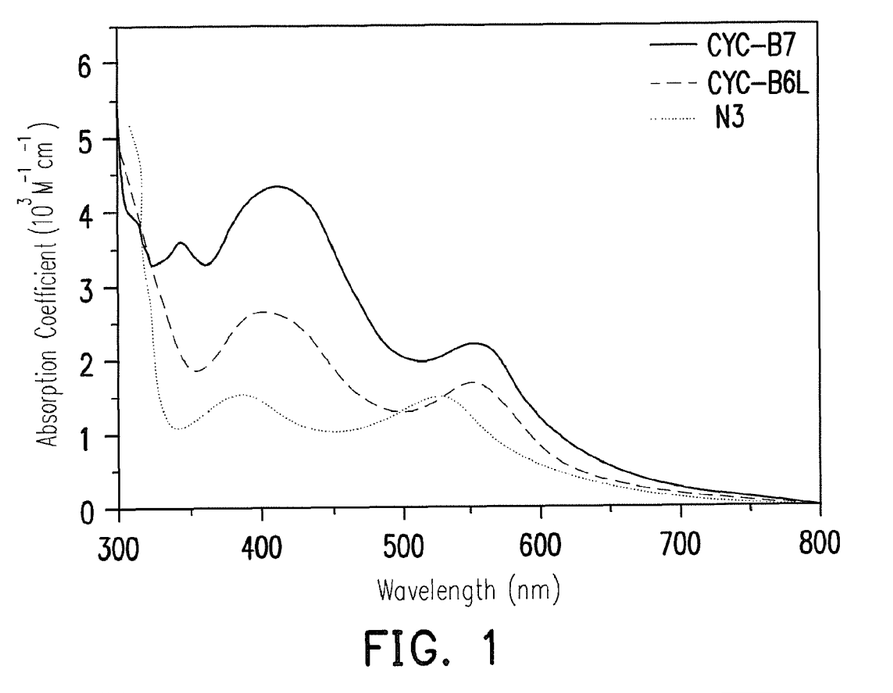
FIG. 1 illustrates the absorption spectrums of the photosensitizer dyes (CYC-B6L and CYC-B7) of the present invention and the conventional photosensitizer dye (N3).
Figure 2:
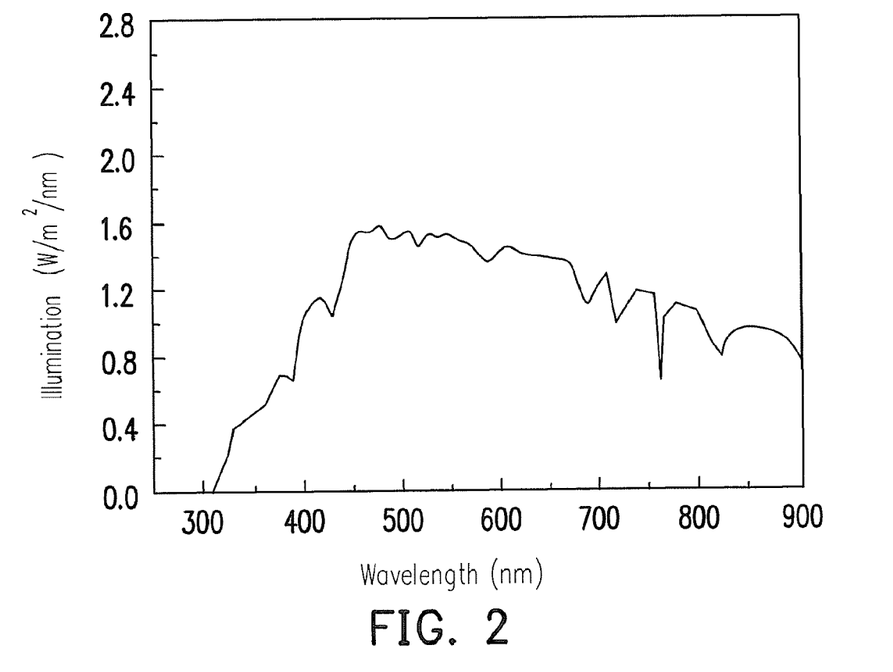
FIG. 2 illustrates the absorption spectrum of solar light.

Further, the absorption spectrums (as shown in FIG. 1) of CYC-B6L, CYC-B7 and N3 are compared with the solar light spectrum (as shown in FIG. 2) mentioned in Annual Book of ASTM Standard, G159-98 Standard tables for references solar spectral irradiance at air mass 1.5: direct normal and hemispherical for a 37° tilted surface, Vol. 14.04 (2003). It is learned that the absorption spectrums of CYC-B6L and CYC-B7 are more similar to the solar light spectrum than the absorption spectrum of N3. Therefore, when the ruthenium-based complex photosensitized dye of the present invention is applied to the DSSC, the cell device has a higher photoelectric conversion efficiency.

Next, the ruthenium-based complex photosensitized dye of the present invention is used as a material of the dye layer in a DSSC for fabricating the DSSC, and the performance of the cell device is measured. The method of fabricating a DSSC in which the material of the dye layer is the CYC-B6L or CYC-B7 dye includes the following steps. First, the prepared TiO$_2$ electrode is dipped in the solution containing the CYC-B6L or CYC-B7 dye for a period of time, and the CYC-B6L or CYC-B7 dye is absorbed to the surface of the TiO$_2$ electrode by self-assembling. Afterwards, the TiO$_2$ electrode is taken out, roughly washed with solvent, dried, capped with a counter electrode and sealed with epoxy resin. Further, the electrolyte (the formulation is 0.6 M 1-methyl-3-propylimidazolium iodide (PMII)/0.05M I$_2$/0.1 M LiI/0.5 M 4-tBP/acetonitrile) is injected and the injection hole is then sealed. The fabrication process of the DSSC is thus completed. After the DSSC including the CYC-B6L or CYC-B7 dye used as a material of the dye layer is completed, the parameters such as voltage, current and photoelectric conversion efficiency are measured, and the measurement results are shown in Table 2.

TABLE 2

| Photosensitizer dye | Short circuit current density Jsc (mA/cm$^2$) | Open circuit voltage Voc (V) | Fill factor (FF) | Photoelectric conversion efficiency η (%) |
|---|---|---|---|---|
| CYC-B6L | 15.7 | 0.710 | 0.664 | 7.42 |
| CYC-B7 | 11.4 | 0.705 | 0.705 | 5.66 |

As shown in Table 2, the photoelectric conversion efficiency of the DSSC including the CYC-6BL dye is 7.42% and that of the DSSC including the CYC-B7 dye is 5.66%. That is, the ruthenium-based complex photosensitizer dye of the present invention has at least one of the special groups represented by formulae (2) to (8), so that the cell device has good photoelectric conversion efficiency when the ruthenium-based complex photosensitizer dye of the present invention is applied to the dye molecule layer of the DSSC.

In summary, the ruthenium-based complex photosensitizer dye of the present invention is characterized in having at least one of the special groups represented by formulae (2) to (8), so that the ruthenium-based complex photosensitizer dye has good light-absorbing ability and the absorption spectrum thereof is similar to the solar light spectrum. Further, the fabricated DSSC including the ruthenium-based complex photosensitizer dye of the present invention has good photoelectric conversion efficiency.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:

1. A photosensitizer dye, being a ruthenium-based complex represented by formula (1):

Formula (1)

wherein in formula (1), $X_1$ is represented by formula (2); and $X_2$ is hydrogen or the same as $X_1$;

Formula (2)

wherein in the formula (2), Ra and Rb are each independently hydrogen, $C_mH_{2m+1}$ with m from 1 to 15 or $OC_pH_{2p+1}$ with p from 1 to 15; and n is from 1 to 4;

wherein in the formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

2. A dye-sensitized solar cell, characterized in using the photosensitizer dyes in claim 1 as a material of a dye layer.

3. A photo sensitizer dye, being a ruthenium-based complex represented by formula (1):

Formula (1)

wherein in formula (1), $X_1$ is represented by formula (3); and $X_2$ is hydrogen or the same as $X_1$;

Formula (3)

wherein in formula (3), Rc is hydrogen or $C_mH_{2m+1}$ with m from 1 to 15; Rd and Re are each independently $C_mH_{2m+1}$ with m from 1 to 15 or $OC_pH_{2p+1}$ with p from 1 to 15; and n is from 1 to 4;

wherein in formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

4. A dye-sensitized solar cell, characterized in using the photosensitizer dyes in claim 3 as a material of a dye layer.

5. A photosensitizer dye, being a ruthenium-based complex represented by formula (1):

Formula (1)

wherein in formula (1), $X_1$ is represented by formula (4); and $X_2$ is hydrogen or the same as $X_1$;

Formula (4)

wherein in formula (4), Rf, Rg and Rh are each independently hydrogen, $C_mH_{2m+1}$ with m from 1 to 15 or $OC_pH_{2p+1}$ with p from 1 to 15; and n is from 1 to 4;

wherein in formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

6. A dye-sensitized solar cell, characterized in using the photosensitizer dyes in claim 5 as a material of a dye layer.

7. A photo sensitizer dye, being a ruthenium-based complex represented by formula (1):

Formula (1)

wherein in formula (1), $X_1$ is represented by formula (5); and $X_2$ is hydrogen or the same as $X_1$;

Formula (5)

wherein in formula (5), Ri, Rj and Rk are each independently hydrogen, $C_mH_{2m+1}$ with m from 1 to 15 or $OC_pH_{2p+1}$ with p from 1 to 15; and n is from 1 to 4;

wherein in formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

8. A dye-sensitized solar cell, characterized in using the photosensitizer dyes in claim 7 as a material of a dye layer.

9. A photo sensitizer dye, being a ruthenium-based complex represented by formula (1):

Formula (1)

wherein in formula (1), $X_1$ is represented by formula (6); and $X_2$ is hydrogen or the same as $X_1$;

Formula (6)

wherein in formula (6), Rl, Rm, Rn and Ro are each independently hydrogen, $C_mH_{2m+1}$ with m from 1 to 15 or $OC_pH_{2p+1}$ with p from 1 to 15; and n is from 1 to 4;
wherein in formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

10. A dye-sensitized solar cell, characterized in using the photosensitizer dyes in claim 9 as a material of a dye layer.

11. A photosensitizer dye, being a ruthenium-based complex represented by formula (1):

Formula (1)

wherein in formula (1), $X_1$ is represented by formula (7); and $X_2$ is hydrogen or the same as $X_1$;

Formula (7)

wherein in formula (7), Rp is hydrogen, $C_mH_{2m+1}$ with m from 1 to 15 or $OC_pH_{2p+1}$ with p from 1 to 15; Rq is $C_mH_{2m+1}$ with m from 1 to 2 or $OC_pH_{2p+1}$ with p from 1 to 15; and n is from 1 to 4;
wherein in formula (1), $Y_1$ is hydrogen, lithium, sodium or a tetra-alkyl ammonium group represented by formula (8); and $Y_2$ is hydrogen or the same as $Y_1$; and Formula (8)

wherein in formula (8), A, B, C and D are each independently hydrogen or $C_mH_{2m+1}$ with m from 1 to 15.

12. A dye-sensitized solar cell, characterized in using one of the photosensitizer dyes in claim 11 as a material of a dye layer.

* * * * *